US005849871A

United States Patent [19]
Cone et al.

[11] Patent Number: 5,849,871
[45] Date of Patent: Dec. 15, 1998

[54] α-MELANOCYTE STIMULATING HORMONE RECEPTOR

[75] Inventors: Roger D. Cone, Oregon City; Kathleen G. Mountjoy, Portland, both of Oreg.

[73] Assignee: Oregon Health Sciences University, Portland, Oreg.

[21] Appl. No.: 466,906

[22] Filed: Jun. 6, 1995

Related U.S. Application Data

[62] Division of Ser. No. 866,979, Apr. 10, 1992, Pat. No. 5,532,347.

[51] Int. Cl.$^6$ .......................... C07K 14/72; C07K 14/68; C12N 15/12; C12N 5/10
[52] U.S. Cl. .......................... 530/350; 530/312; 530/306; 435/325; 435/252.3; 435/254.11; 435/69.1; 435/320.1
[58] Field of Search .......................... 530/350, 306, 530/312; 435/325, 320.1, 69.1, 252.3, 254.11

[56] References Cited

U.S. PATENT DOCUMENTS

| | | | |
|---|---|---|---|
| 4,650,764 | 3/1987 | Temin et al. | 435/240 |
| 4,683,195 | 7/1987 | Mullis et al. | 435/6 |
| 4,683,202 | 7/1987 | Mullis | 435/91 |
| 4,761,371 | 8/1988 | Bell et al. | 435/68 |
| 4,861,719 | 8/1989 | Miller | 435/236 |
| 5,532,347 | 7/1996 | Cone et al. | 536/23.5 |

OTHER PUBLICATIONS

Ghanem et al., Evidence for alpha–melanocyte–stimulating hormone (alpha–MSH) receptors on human malignant melanoma cells, Int. J. Cancer, 41: 248–255, Feb. 1988.
Hanneman et al., In Peptide Hormones as Prohormones, Martinez, ed. (Ellis Horwood, Ltd: Chichester, UK), pp. 53–82.
DeWied & Jolles, 1982, Physiol. Rev. 62: 976–1059.
Shimuze, 1985, Yale J. Biol. Med. 58: 561,570.
Tatro & Rechlin, 1987, Endocrinology 121: 1900–1907.
Solca et al., 1989, J. Biol. Chem. 264: 14277–14280.
Gerst et al., 1987, Mol. Pharmacol. 31:81.
Libert et al., 1989, Science 244: 569.
Zhou et al., 1990, Nature 347: 78–80.
Masau et al., 1987, Nature 329: 836.
Applebury & Hargrave, 1986, Vision Res. 26:1881–1895.
Bertling, 1987, Bioscience Reports 7:107–112.
Buckley & Ramachandran, 1981, PNAS USA 78:7431–7435.
Bunzow et al., 1988, Nature 336:783–787.
Chen & Okayama, 1987, Mol. Cell Biol. 7:2745–2752.
Chirgwin et al., 1979, Biochemistry 18:5294–5299.
Dixon et al., 1987, EMBO J. 6:3269–3275.
Gilman, 1970, PNAS USA 67:305–312.
Grahane–Smith et al., 1967, J. Biol. Chem. 242:5535–5541.
Karnik et al., 1988, PNAS USA 85:8459–8463.
Kyte & Doolittle, 1982, J. Mol. Biol. 157:105–132.
Liebert et al., 1989, Science 244:569–572.
Matsuda, 1990, Nature 346:561–564.
Mertz & Catt, 1991, PNAS USA 88:8525–8529.
Pawalek et al., 1976, Invest., Dermatol. 66:200–209.
Pawalek, 1985, Yale J. Biol. Med. 58:571–578.
Probst, et al., DNA & Cell Biol. 11:1–20.
Saiki et al., 1988, Science 239:487–491.
Sanger et al., 1977., Proc. Natl. Acad Sci. USA 74:5463–5467.
Siegrist et al., 1991, J. Receptor Res. 11:323–331.
Slominski et al., 1992, Life Sci. 50:1103–1108.
Smithies et al., 1985, Nature 317:230–234.
Spindel et al., 1990, Mol Endocrinol. 4:1956–1963.
Tatro et al., 1990, Cancer Res. 50:1237–1242.
Thomas and Capecchi, 1987, Cell 51:503–512.
Zubay, Biochemistry (2ed), 1988 (MacMillen Publ. NY) p. 33.

*Primary Examiner*—Stephen Walsh
*Assistant Examiner*—Claire M. Kaufman
*Attorney, Agent, or Firm*—McDonnell Boehnen Hulbert & Berghoff

[57] ABSTRACT

The present invention relates to a mammalian alpha–melanocyte stimulating hormone receptor. The invention is directed toward the isolation, characterization and pharmacological use of mammalian melanocyte stimulating hormone receptor, the gene corresponding to this receptor, a recombinant eukaryotic expression construct capable of expressing a mammalian melanocyte stimulating hormone receptor in cultures of transformed eukaryotic cells and such cultures of transformed eukaryotic cells that synthesize mammalian melanocyte stimulating hormone receptor. The invention also provides methods for screening MSH-R agonists and antagonists in vitro using preparations of receptor from such cultures of eukaryotic cells transformed with a recombinant eukaryotic expression construct comprising the MSH-R receptor gene. The invention specifically provides human and mouse MSH-R genes.

9 Claims, 12 Drawing Sheets

FIG. 1A

```
         10         20         30         40         50         60         70
TTCCTGACAA GACTATGTCC ACTCAGGAGC CCCAGAAGAG TCTTCTGGGT TCTCTCAACT CCAATGCCAC
         80         90        100        110        120        130        140
CTCTCACCTT GGACTGGCCA CCAACCAGTC AGAGCCTTGG TGCCTGTATG TGTCCATCCC AGATGGCCTC
        150        160        170        180        190        200        210
TTCCTCAGCC TAGGGCTGGT GAGTCTGGTG GAGAATGTGC TGGTTGTGAT AGCCATCACC AAAAACCGCA
        220        230        240        250        260        270        280
ACCTGCACTC GCCCATGTAT TACTTCATCT GCTGCCTGGC CCTGTCTGAC CTGATGGTAA GTGTCAGCAT
        290        300        310        320        330        340        350
CGTGCTGGAG ACTACTATCA TCCTGCTGCT GGAGGTGGGC ATCCTGGTGG CCAGAGTGGC TTTGGTGCAG
        360        370        380        390        400        410        420
CAGCTGGACA ACCTCATTGA CGTGCTCATC TGTGGCTCCA TGGTGTCCAG TCTCTGCTTC CTGGGCATCA
        430        440        450        460        470        480        490
TTGCTATAGA CCGCTACATC TCCATCTTCT ATGCGCTGCG TTATCACAGC ATCGTGACGC TGCCCAGAGC
        500        510        520        530        540        550        560
ACGACGGGCT GTCGTGGGCA TCTGGATGGT CAGCATCGTC TCCAGCACCC TCTTTATCAC CTACTACAAC
```

FIG. 1B

```
       570        580        590        600        610        620        630
CACACAGCCCG TTCTGCTTCTG CCTCGTCACT TTCTTTCTAG CCATGCTGGC ACTCATGGCG ATTCTGTATG
       640        650        660        670        680        690        700
CCCACATGTT CACGAGAGCG TGCCAGCACG TCCAGGGCAT TGCCCAGCTC CACAAAAGGC GGCGGTCCAT
       710        720        730        740        750        760        770
CCGCCAAGGC TTCTGCCTCA AGGGTGCTGC CACCCTTACT ATCCTTCTGG GGATTTTCTT CCTGTGCTGG
       780        790        800        810        820        830        840
GGCCCCTTCT TCCTGCATCT CTTGCTCATC GTCCTCTGCC CTCAGCACCC CACCTGCAGC TGCATCTTCA
       850        860        870        880        890        900        910
AGAACTTCAA CCTCTTCCTC CTCCTCATCG TCCTCAGCTC CACTGTTGAC CCCCTCATCT ATGCTTTCCG
       920        930        940        950        960        970        980
CAGCCAGGAG CTCCGCATGA CACTCAAGGA GGTGCTGCTG TGCTCCTGGT GATCAGAGGG CGCTGGGCAG
       990       1000       1010       1020       1030       1040       1050
AGGGTGACAG TGATATCCAG TGGCCCTGCAT CTGTGAGACC ACAGGTACTC ATCCCCTTCCT GATCTCCATT
      1060       1070       1080       1090       1100       1110       1120
TGTCTAAGGG TCGACAGGAT GAGCTTTAAA ATAGAAACCC AGAGTGCCTG GGGCCAGGAG AAAGGGTAAC
```

FIG. 1C

```
           1130       1140       1150       1160       1170       1180       1190
      TGTGACTGCA GGGCTCACCC AGGGCAGCTA CGGGAAGTGG AGGAGACAGG GATGGGAACT CTAGCCCTGA
           1200       1210       1220       1230       1240       1250       1260
      GCAAGGGTCA GACCACAGGC TCCTGAAGAG CTTCACCTCT CCCCACCTAC AGGCAACTCC TGCTCAAGCC
```

FIG. 1D

```
         10          20         30         40         50         60         70
CCCGCATGTG  GCCGCCCTCA ATGGAGGGCT CTGAGAACGA CTTTTAAAAC GCAGAGAAAA AGCTCCATTC
         80          90        100        110        120        130        140
TTCCCAGACC  TCAGCGCAGC CCTGGCCAGC GAAGGCAGGA GACAGAGGCC AGGACGGTCC AGAGGTGTCG
        150         160        170        180        190        200        210
AAATGTCCTG  GGAACCTCAG CAGCAGCCAC CAGGGAAGAG GCAGGGAGGG AGCTGAGGAC CAGGCTTGGT
        220         230        240        250        260        270        280
TGTGAGAATC  CCTGACCCCA GGCGGGTTGAT GCCAGGAGGT GTCTGGACTG GCTGCCGCCAT GCCTGGGCTG
        290         300        310        320        330        340        350
ACCTGTCCAG  CCAGGCAGAG GGTGTGAGGG CAGATCTGGG GGTGCCCAGA TGGAAGGAGG CAGGCATGCG
        360         370        380        390        400        410        420
GACACCCAAG  GCCCCCTGGC AGCACCATGA ACTAAGCAGG ACACCTGGAG GGGAAGAACT CTGGGGACCT
```

FIG. 1E

```
     430        440        450        460        470        480        490
GGAGGCCTCC AACGACTCCT TCCTGCTTCC TGGACAGGAC TATGGCTGTC CAGGGATCCC AGAGAAGACT 500        510        520        530        540        550        560
TCTGGGCTCC CTCAACTCCA CCCCCACAGC CATCCCCCAG CTGGGGCTGG CTGCCAACCA GACAGGAGCC 570        580        590        600        610        620        630
CGGTGCCTGG AGGTGTCCAT CTCTGACGGG CTCTTCCTCA GCCTGGGGCT GGTGAGCTTC GTGGAGAACG 640        650        660        670        680        690        700
CGCTGGTGGT GCCCACCATC GCCAAGAACC GGAACCTGCA CTCACCCATC TACTGCTTCA TCTGCTGCCT 710        720        730        740        750        760        770
GGCCTTGTCG GACCTGCTGG TGAGCGGGAC GAACGTGCTG GAGACGGCCG TCATCCCTCCT GCTGGAGGCC 780        790        800        810        820        830        840
GGTGCACTGG TGGCCCGGGC TGCGGTGCTG CAGCAGCTGG ACAATGTCAT TGACGTGATC ACCTGCAGCT 850        860        870        880        890        900        910
CCATGCTGTC CAGCCTCTGC TTCCTGGGCG CCATCGCCGT GGACCGCTAC ATCTCCATCT TCTACGCACT 920        930        940        950        960        970        980
GCGCTACCAC AGCATCGTGA CCCTGCCCGC GGGCCCGCGA GCCGTTGCGG GCCGTTGCGG CCATCTGGGT GGCCAGTGTC
```

FIG. 1F

```
      990       1000       1010       1020       1030       1040       1050
GTCTTCAGCA CGCTCTTCAT CGCCTACTAC CACCACGTGG CCGTCCTGCT GTGCCTCGTG CTCTTCTTCC 1060       1070       1080       1090       1100       1110       1120
TGGCTATGCT GGTGCTCATG GCCGTGCTGT ACGTCCACAT GCTGGCCCGG GCCTGCCAGC ACGCCCAGGG 1130       1140       1150       1160       1170       1180       1190
CATCGCCCGG CTCCACAAGA GGCAGCGCCC GGTCCACCAG GGCTTTGGCC TTAAAGGCGC TGTCACCCTC 1200       1210       1220       1230       1240       1250       1260
ACCATCCTGC TGGGCATTTT CTTCCTCTGC TCGGGCCCCT TCTTCCTGCA TCTCACACTC ATCGTCCTCT 1270       1280       1290       1300       1310       1320       1330
GCCCCGAGCA CCCCACGTGC GGCTGCATCT TCAAGAACTT CAACCTCTTT CTCGCCCCTC TCATCTGCAA 1340       1350       1360       1370       1380       1390       1400
TGCCATCATC GACCCCCTCA TCTACGCCTT CCACAGCCAG GAGCTCCGCA GCACGCTCAA GGAGGTGCTG 1410       1420       1430       1440       1450       1460       1470
ACATGCTCCT GGTGAGCGCG CTGCACGCGC TTTAAGTGTG CTGGGCAGAG GGAGGTGGTG ATATTGTGGT 1480       1490       1500       1510       1520       1530       1540
CTGGTTCCTG TGTGACCCTG GGCAGTTCCT TACCTCCCTG GTCCCCGTTT GTCAAAGACG ATGGACTAAA
```

FIG. 1G

```
     1550       1560       1570       1580       1590       1600       1610
TGATCTCTGA AAGTGTTGAA GCGCGGACCC TTCTGGGCAG GGAGGGGTCC TGCAAAACTC CAGGCAGGAC 1620       1630
TTCTCACCAG CAGTCGTGGG AAC
```

FIG. 2A

```
MOUSE MSH-R                                                          mstQepQkaLvGSLNSnaTah--     21
HUMAN MHS-R                                                          mavQgsQrrLlGSLNStpTaipq     23
HUMAN ACTH-R                                                                       mkhiinsye      9
RAT CANNAB.                                                     m-(101)-----------------        102

I
MOUSE MSH-R   LGLATNQsepwCLyVSIPDGLFLSLGLVSLVENvLVViAItKNRNLHcPMYyFICCLALSD                      82
HUMAN MHS-R   LGLAaNQtgarCLeVSIsDGLFLSLGLVSLVENaLVVatIaKNRNLHsPMYcFICCLALSD                      84
HUMAN ACTH-R  ninnTarnnadCprVvlPeeiFfTisiVgvlENliVl1AvfKNkNLqaPMYfFICsLAiSD                      70
RAT CANNAB.   ----------------L-LtLg---VLENLLVL--I---R-L--P-Y-FI-SLA---D                       163

II
MOUSE MSH-R   LmVSvsiVLETtiILLLEvGiLVARvAlvQQLDNIIDVliCgSMvSSLCFLGiIAiDRYIS                     143
HUMAN MHS-R   -LLVSgtnVLETaviLLLEaGaLVARaAvlQQLDNvIDVitCsSMLSSLCFLGaiAvDRYIS                    145
HUMAN ACTH-R  mLgSlykiLEniliLrnmGyLkpRgsfettaDdiIDslfvlsLlgSifsLsvIAaDRYIt                      131
RAT CANNAB.   LLGSV--V-----------------F----------------V----GSLF-L---AIDRYIS                  224
                                   III
```

FIG. 2B

```
                        IV                                                                              V
MOUSE MSH-R    IFYALRYHSIVTLPRArRAVvgIWmvSivsSTLFItyYkhtAVLLCLVtFFLAMLaIMAiL   204
HUMAN MHS-R    -IFYALRYHSIVTLPRARRAVvgIWmvSivsSTLFItyYkhtAVLLCLVtFFLAMLaIMAiL   206
HUMAN ACTH-R   IFhALRYHSIVTmrRtvvvltviWTfctgtgitmvifshHVptvitftslFplMLVfilcL   192
RAT CANNAB.    I----L--Y---IVT-P-AVVA-----WT--IV---L--------------FPL-----L--   285
                                                                V
                        V                                                              VI
MOUSE MSH-R    YaHMFtRACQHvQGIAqLHKRQRsirQGFsLKGAaTLTILLGIFFLCWGPFFLHLLIVLC-   264
HUMAN MHS-R    -YVHMLaRACQHaQGIARLHKRQRPvhQGFgLKGAVtLTILLGIFFLCWGPFFLHLtLIVLC-   266
HUMAN ACTH-R   YVHMF------lIARsHtRkistlpranmKGAiTLTILLGvFifCWaPFvLHVLLmtfC-   245
RAT CANNAB.    ---------(31)----RP-----R-----A-TL---L-V-I-CWGP----------   373
                                        VII
MOUSE MSH-R    PqHPTCaCIFKNFNLFLLLIvlsstvDPLIYAFRSQELRmTLKEVLlCS--W   317
HUMAN MHS-R    -PeHPTCg-CIFKNFNLFLLLIvlsstvDPLIYAFhSQELRmTLKEVLtCS--W   316
HUMAN ACTH-R   PsnPyCaCymslFqvngMLImCNAvIDPFIYAFRSpKLRdafKkmifCSryW   297
RAT CANNAB.    -------I----F-----ML--LNSTV-P--IYA-RS--LR-AF--M-F-S--(56)   483
```

α-MELANOCYTE STIMULATING HORMONE RECEPTOR

This application is a divisional application of U.S. Ser. No. 07/866,979, filed Apr. 10, 1992, now U.S. Pat. No. 5,532,347, issued Jul. 2, 1996.

This invention was made with government support under 1R01DK41921-03, 1R01DK43859-01, and 1P01DK44239-10A1 by the National Institutes of Health. The government has certain rights in the invention.

BACKGROUND OF THE INVENTION

1. Field of the Invention

This invention relates to melanocyte stimulating hormone receptors from mammalian species and the genes corresponding to such receptors. Specifically, the invention relates to the isolation, cloning and sequencing of a human melanocyte stimulating hormone receptor gene. The invention also relates to the isolation, cloning and sequencing of a mouse melanocyte stimulating hormone receptor gene. The invention relates to the construction of eukaryotic recombinant expression constructs capable of expressing these melanocyte stimulating hormone receptors in cultures of transformed eukaryotic cells, and the production of the melanocyte stimulating hormone receptor in such cultures. The invention relates to the use of such cultures of transformed eukaryotic cells to produce homogeneous compositions of such melanocyte stimulating hormone receptors. The invention also provides cultures of such cells producing melanocyte stimulating hormone receptor for the characterization of novel and useful drugs. Antibodies against and epitopes of these melanocyte stimulating hormone receptor proteins are also provided by the invention.

2. Background of the Invention

The proopiomelanocortin (POMC) gene product is processed to produce a large number of biologically active peptides. Two of these peptides, α-melanocyte stimulating hormone (αMSH), and adrenocorticotropic hormone (ACTH) have well understood roles in control of melanocyte and adrenocortical function, respectively. Both of these hormones, however, are found in a variety of forms with unknown functions. The melanocortin peptides also have a diverse array of biological activities in other tissues, including the brain, and immune system, and bind to specific receptors there with a distinct pharmacology (see, Hanneman et al., in *Peptide Hormone as Prohormones*, G. Martinez, ed. (Ellis Horwood Ltd.: Chichester, UK) pp. 53–82; DeWied & Jolles, 1982, *Physiol. Rev.* 62: 976–1059for reviews).

A complete understanding of these peptides and their diverse biological activities requires the isolation and characterization of their corresponding receptors. Some biochemical studies have been reported in the prior art.

Shimuze, 1985, Yale *J. Biol. Med.* 58: 561–570 discusses the physiology of melanocyte stimulating hormone.

Tatro & Reichlin, 1987, *Endocrinology* 121: 1900–1907 disclose that MSH receptors are widely distributed in rodent tissues.

Solca et al., 1989, *J. Biol. Chem.* 264: 14277–14280 disclose the molecular weight characterization of mouse and human MSH receptors linked to radioactivity and photoaffinity labeled MSH analogues.

Siegrist et al., 1991, *J. Receptor Res.* 11: 323–331 disclose the quantification of receptors in mouse melanoma tissue by receptor autoradiography.

The present invention comprises a human melanocyte stimulating hormone receptor gene, the nucleotide sequence of this gene and the deduced amino acid sequence of its cognate protein, a homogeneous composition of the melanocyte stimulating hormone receptor, nucleic acid hybridization probes and a method for determining the tissue distribution of expression of the gene, a recombinant expression construct capable of expressing the gene in cultures of transformed eukaryotic cells, and such cultures of transformed eukaryotic cells useful in the characterization of novel and useful drugs. The present invention also comprises the homologue of the human melanocyte stimulating hormone receptor gene from the mouse.

BRIEF DESCRIPTION OF THE DRAWINGS

FIGS. 1A through 1G illustrate the nucleotide sequence of the mouse (FIGS. 1A through 1C; SEQ ID NO:3) and human (FIGS. 1D through 1G; SEQ ID NO:5) melanocyte stimulating hormone receptor, respectively.

FIGS. 2A and 2B present an amino acid sequence comparison between the mouse (SEQ ID NO:4) and human (SEQ ID NO:6) melanocyte stimulating hormone receptor proteins, and with human ACTH receptor (SEQ ID NO:7) and rat cannabinoid receptor (SEQ ID NO:8).

SUMMARY OF THE INVENTION

Figure 3:
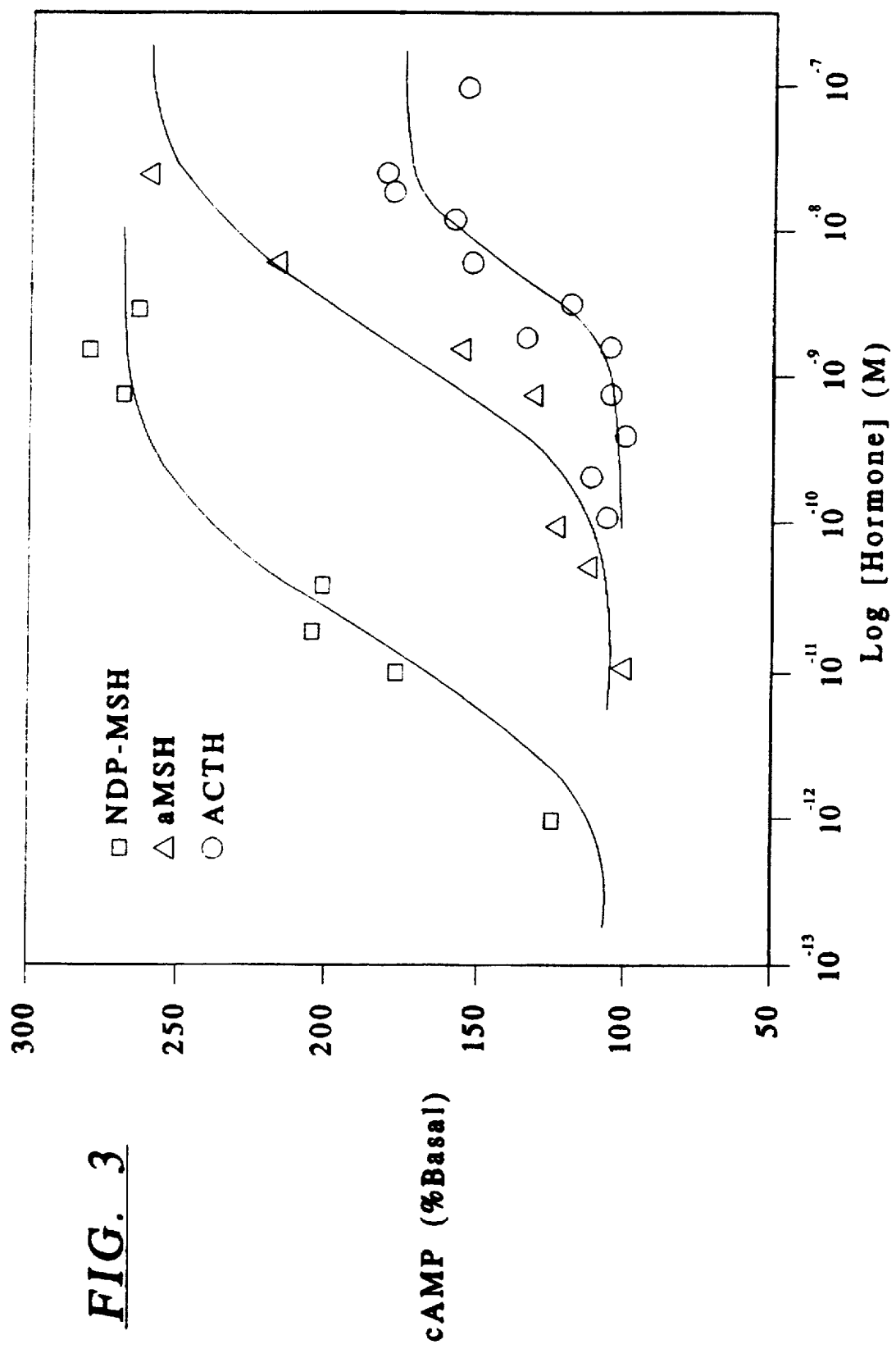
FIG. 3 illustrates binding of melanocyte stimulating hormone receptor agonists to mouse melanocyte stimulating hormone receptor expressed in human 293 cells.

The present invention relates to the cloning, expression and functional characterization of mammalian melanocyte stimulating hormone receptor (MSH-R) genes. The invention comprises the nucleotide sequence of these genes encoding the mammalian MSH-Rs and the deduced amino acid sequences of the cognate proteins, as well as tissue distribution patterns of expression of these genes.

In particular, the present invention is directed toward the isolation, characterization and pharmacological use of the human MSH-R, the gene corresponding to this receptor, a nucleic acid hybridization probe comprising DNA sequences of the human MSH-R, a recombinant eukaryotic expression construct capable of expressing the human MSH-R in cultures of transformed eukaryotic cells and such cultures of transformed eukaryotic cells that synthesize the human MSH-R, a homogeneous composition of the human MSH-R, and antibodies against and epitopes of the human MSH-R.

The present invention is also directed toward the isolation, characterization and pharmacological use of the mouse MSH-R, the gene corresponding to this receptor, a nucleic acid hybridization probe comprising DNA sequences of the mouse MSH-R, a recombinant eukaryotic expression construct capable of expressing the mouse MSH-R in cultures of transformed eukaryotic cells and such cultures of transformed eukaryotic cells that synthesize the mouse MSH-R, a homogeneous composition of the mouse MSH-R, and antibodies against and epitopes of the mouse MSH-R.

It is an object of the invention to provide a nucleotide sequence encoding a mammalian MSH-R. In a preferred embodiment of the invention, the nucleotide sequence encodes the human MSH-R. In another preferred embodiment, the nucleotide sequence encodes the mouse MSH-R.

The present invention includes a nucleotide sequence encoding a human MSH-R receptor derived from a DNA molecule isolated from a human genomic library (SEQ ID NO:5). In this embodiment of the invention, the nucleotide sequence includes 1635 nucleotides of the human MSH-R gene comprising 953 nucleotides of coding sequence, 462 nucleotides of 5' untranslated sequence and 220 nucleotides of 3' untranslated sequence.

The present invention also includes a nucleotide sequence encoding a mouse MSH-R derived from a cDNA molecule isolated from a cDNA library constructed with RNA from mouse Cloudman melanoma cells (SEQ ID NO:3). In this embodiment of the invention, the nucleotide sequence includes 1260 nucleotides of the mouse MSH-R gene comprising 947 nucleotides of coding sequence, 15 nucleotides of 5' untranslated sequence and 298 nucleotides of 3' untranslated sequence.

The invention includes nucleotide sequences of mammalian MSH-Rs, most preferably mouse and human MSH-Rs (SEQ ID NOs:3&5), and includes allelic variations of these nucleotide sequences and the corresponding MSH-R molecule, either naturally occurring or the product of in vitro chemical or genetic modification, each such variant having essentially the same nucleotide sequence as the nucleotide sequence of the corresponding MSH-R disclosed herein, wherein the resulting MSH-R molecule has substantially the same biological properties as the MSH-R molecule corresponding to the nucleotide sequence described herein. The term "substantially homologous to" as used in this invention encompasses such allelic variability as described in this paragraph.

The invention also includes a predicted amino acid sequence for the mouse (SEQ ID NO:4) and human (SEQ ID NO:6) MSH-R deduced from the nucleotide sequence comprising the complete coding sequence of the mouse (SEQ ID NO:3) and human (SEQ ID NO:5) MSH-R gene as described herein.

In another aspect, the invention comprises a homogeneous composition of a 35.3 kilodalton mouse MSH-R or derivative thereof, wherein the amino acid sequence of the MSH-R or derivative thereof comprises the mouse MSH-R sequence shown in FIG. 2 (SEQ ID NO:4).

In another aspect, the invention comprises a homogeneous composition of a 34.7 kilodalton human MSH-R or derivative thereof, wherein the amino acid sequence of the MSH-R or derivative thereof comprises the human MSH-R sequence shown in FIG. 2 (SEQ ID NO:6).

This invention provides both nucleotide and amino acid probes derived from these sequences. The invention includes probes isolated from either cDNA or genomic DNA clones, as well as probes made synthetically with the sequence information derived therefrom. The invention specifically includes but is not limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide sequences of mammalian MSH-R, preferably the mouse or human MSH-R, for use as nucleic acid hybridization probes to determine the pattern, amount and extent of expression of this receptor in various tissues of mammals, including humans. It is also an object of the present invention to provide nucleic acid hybridization probes derived from the sequences of the mouse or human MSH-R to be used for the detection and diagnosis of genetic diseases. It is an object of this invention to provide nucleic acid hybridization probes derived from the DNA sequences of the mouse or human MSH-R to be used for the detection of novel related receptor genes.

The present invention also includes synthetic peptides made using the nucleotide sequence information comprising cDNA or genomic clone embodiments of the invention. The invention includes either naturally occurring or synthetic peptides which may be used as antigens for the production of MSH-R-specific antibodies, or used for competitors of the MSH-R molecule for drug binding, or to be used for the production of inhibitors of the binding of agonists or antagonists or analogues thereof to a MSH-R molecule.

The present invention also provides antibodies against and epitopes of mammalian MSH-Rs, preferably mouse or human MSH-R proteins. It is an object of the present invention to provide antibodies that are immunologically reactive to a mammalian MSH-R protein. It is a particular object of the invention to provide monoclonal antibodies to mammalian MSH-R protein, most preferably mouse or human MSH-R protein.

It is also an object of the present invention to provide a hybridoma cell line that produces such an antibody. It is a particular object of the invention to provide a hybridoma cell line that is the result of fusion between a non-immunoglobulin producing mouse myeloma cell line and spleen cells derived from a mouse immunized with a human cell line which expresses an MSH-R antigen. The present invention also provides a hybridoma cell line that produces such an antibody, and that can be injected into a living mouse to provide an ascites fluid from the mouse that is comprised of such an antibody.

The present invention also provides a pharmaceutical composition comprising a therapeutically effective amount of a monoclonal antibody that is immunologically reactive to a mammalian MSH-R, preferably a mouse or human MSH-R, and in a pharmaceutically acceptable carrier.

It is a further object of the present invention to provide an epitope of a mammalian MSH-R protein wherein the epitope is immunologically reactive to an antibody specific for the mammalian MSH-R. In preferred embodiments, the epitope is derived from mouse or human MSH-R protein.

It is another object of the invention to provide a chimeric antibody that is immunologically reactive to a mammalian MSH-R protein. In a preferred embodiment, the chimeric antibody is a monoclonal antibody. In a preferred embodiment, the MSH-R is a mouse or human MSH-R.

The present invention provides a recombinant expression construct comprising the nucleotide sequence of a mammalian MSH-R, preferably the mouse or human MSH-R and sequences sufficient to direct the synthesis of mouse or human MSH-R in cultures of transformed eukaryotic cells. In a preferred embodiment, the recombinant expression construct is comprised of plasmid sequences derived from the plasmid pcDNA/neo and cDNA or genomic DNA of mouse or human MSH-R gene. This invention includes a recombinant expression construct comprising essentially the nucleotide sequences of genomic or cDNA clones of mouse or human MSH-R in an embodiment that provides for their expression in cultures of transformed eukaryotic cells.

It is also an object of this invention to provide cultures of transformed eukaryotic cells that have been transformed with such a recombinant expression construct and that synthesize mammalian, preferably mouse or human, MSH-R protein. In an additional preferred embodiment, the invention provides human 293 cells that synthesize mouse MSH-R. In an additional preferred embodiment, the invention provides human 293 cells that synthesize human MSH-R protein.

The present invention also includes protein preparations of mammalian, preferably mouse or human MSH-R, and preparations of membranes containing mammalian MSH-R, derived from cultures of transformed eukaryotic cells. In a preferred embodiment, cell membranes containing mouse MSH-R protein are isolated from 293 cell cultures transformed with a recombinant expression construct that directs the synthesis of mouse MSH-R. In another preferred embodiment, cell membranes containing human MSH-R protein are isolated from 293 cell cultures transformed with a recombinant expression construct that directs the synthesis of human MSH-R.

It also an object of this invention to provide mammalian, preferably mouse or human MSH-R for use in the in vitro screening of novel MSH-R agonist and antagonist compounds. In a preferred embodiment, membrane preparations containing the mouse MSH-R, derived from cultures of transformed eukaryotic cells, are used to determine the drug dissociation properties of various novel MSH-R agonist and antagonist compounds in vitro. In another preferred embodiment, membrane preparations containing the human MSH-R, derived from cultures of transformed eukaryotic cells, are used to determine the drug dissociation properties of various novel MSH-R agonist and antagonist compounds in vitro. These properties are then used to characterize such novel compounds by comparison to the binding properties of known mouse or human MSH-R agonists and antagonists.

The present invention will also be useful for the in vivo detection of analogues of agonists or antagonists of MSH-R, known or unknown, either naturally occurring or as the embodiments of a drug.

It is an object of the present invention to provide a method for the quantitative detection of agonists or antagonists, or analogues thereof, of MSH-R, known or unknown, either naturally occurring or as the embodiments of a drug. It is an additional object of the invention to provide a method to detect such agonists, antagonists, or analogues thereof in blood, saliva, semen, cerebrospinal fluid, plasma, lymph, or any other bodily fluid.

Specific preferred embodiments of the present invention will become evident from the following more detailed description of certain preferred embodiment and the claims.

DETAILED DESCRIPTION OF THE PREFERRED EMBODIMENTS

The term "melanocyte stimulating hormone receptor" (MSH-R) as used herein refers to proteins substantially homologous to, and having substantially the same biological activity as, the protein coded for by the nucleotide sequence depicted in FIG. 1 (SEQ ID NO:3). This definition is intended to encompass natural allelic variations in the melanocyte stimulating hormone receptor sequence. Cloned genes of the present invention may code for MSH-R of any species of origin, including, for example, mouse, rat, rabbit, cat, and human, but preferably code for receptors of mammalian, most preferably mouse and human, origin.

Nucleic acid hybridization probes provided by the invention comprise DNA sequences that are substantially homologous to the DNA sequences in FIGS. 1A (SEQ ID NO:3) and 1B (SEQ ID NO:5). Nucleic acid probes are useful for detecting MSH-R gene expression in cells and tissues using techniques well-known in the art, including but not limited to Northern blot hybridization, in situ hybridization and Southern hybridization to reverse transcriptase—polymerase chain reaction product DNAs. The probes provided by the present invention, including oligonucleotide probes derived therefrom, are useful for Southern hybridization of mammalian, preferably human, genomic DNA for screening for restriction fragment length polymorphism (RFLP) associated with certain genetic disorders.

The production of proteins such as the MSH-R from cloned genes by genetic engineering is well known. See, e.g., U.S. Pat. No. 4,761,371 to Bell et al. at Col. 6 line 3 to Col. 9 line 65. (The disclosure of all U.S. patent references cited herein is to be incorporated herein by reference.) The discussion which follows is accordingly intended as an overview of this field, and is not intended to reflect the full state of the art.

DNA which encodes the MSH-R may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the MSH-R gene sequence information provided herein. Probes may be labeled with a detectable group such as a fluorescent group, a radioactive atom or a chemiluminescent group in accordance with known procedures and used in conventional hybridization assays, as described in greater detail in the Examples below. In the alternative, MSH-R gene sequences may be obtained by use of the polymerase chain reaction (PCR) procedure, with the PCR oligonucleotide primers being produced from the MSH-R gene sequence provided herein. See U.S. Pat. Nos. 4,683,195 to Mullis et al. and 4,683,202 to Mullis.

The MSH-R may be synthesized in host cells transformed with a recombinant expression construct comprising a DNA sequence encoding the MSH-R. Such a recombinant expression construct can also be comprised of a vector that is a replicable DNA construct. Vectors are used herein either to amplify DNA encoding the MSH-R and/or to express DNA which encodes the MSH-R. For the purposes of this invention, a recombinant expression construct is a replicable DNA construct in which a DNA sequence encoding the MSH-R is operably linked to suitable control sequences capable of effecting the expression of the MSH-R in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is the plasmid pcDNAI/neo. Transformed host cells are cells which have been transformed or transfected with recombinant expression constructs made using recombinant DNA techniques and comprising a mammalian MSH-R. Transformed host cells may ordinarily express the mammalian MSH-R, but host cells transformed for purposes of cloning or amplifying nucleic acid hybridization probe DNA need not express the receptor. When expressed, the mammalian MSH-R will typically be located in the host cell membrane.

DNA regions are operably linked when they are functionally related to each other. For example: a promoter is operable linked to a coding sequence if it controls the transcription of the sequence; a ribosome binding site is operably linked to a coding sequence if it is positioned so as to permit translation. Generally, operably linked means contiguous and, in the case of leader sequences, contiguous and in the same translational reading frame.

Cultures of cells derived from multicellular organisms are a desirable host for recombinant MSH-R synthesis. In principal, any higher eukaryotic cell culture is workable, whether from vertebrae or invertebrate culture. However, mammalian cells are preferred, as illustrated in the Examples. Propagation of such cells in cell culture has become a routine procedure. See Tissue Culture, Academic Press, Kruse & Patterson, editors (1973). Examples of useful host cell lines are human 293 cells, VERO and HeLa cells, Chinese hamster ovary (CHO) cell lines, and WI138, BHK, COS-7, CV, and MDCK cell lines. Human 293 cells are preferred. Expression vectors for such cells ordinarily include (if necessary) an origin of replication, a promoter located upstream from the gene to be expressed, along with a ribosome binding site, RNA splice sites (if intron-containing genomic DNA is used), a polyadenylation site, and a transcriptional termination sequence.

An origin of replication may be provided either by construction of the vector to include an exogenous origin, such as may be derived from SV40 or other viral source (e.g., polyoma, adenovirus, VSV, or MPV), or may be provided by the host cell chromosomal replication mechanism. If the vector is integrated into the host cell chromosome, the latter may be sufficient.

The invention provides homogeneous compositions of mammalian MSH-R protein produced by transformed eukaryotic cells as provided herein. Such homogeneous compositions are intended to be comprised of mammalian MSH-R protein that comprises 90% of the protein in such homogenous composition.

Mammalian MSH-R protein made from cloned genes in accordance with the present invention may be used for screening agonist compounds for MSH-R activity, or for determining the amount of a MSH-R agonist or antagonist drug in a solution (e.g., blood plasma or serum). For example, host cells may be transformed with a recombinant expression construct of the present invention. MSH-R expressed in that host, the cells lysed, and the membranes from those cells used to screen compounds for MSH-R binding activity. Competitive binding assays in which such procedures may be carried out are well known in the art. By selection of host cells which do not ordinarily express MSH-Rs, pure preparations of membranes containing MSH-Rs can be obtained. Further, MSH-R agonists and antagonists can be identified by transforming host cells with vectors of the present invention. Membranes obtained from such cells can be used in binding studies wherein the drug dissociation activity is monitored.

The recombinant expression constructs of the present invention are useful in molecular biology to transform cells which do not ordinarily express the MSH-R to thereafter express this receptor. Such cells are useful as intermediates for making cell membrane preparations useful for receptor binding assays, which are in turn useful for drug screening. Further, genes and vectors comprising the recombinant expression construct of the present invention are useful in gene therapy. For such purposes, retroviral vectors as described in U.S. Pat. No. 4,650,764 to Temin & Watanabe or U.S. Pat. No. 4,861,719 to Miller may be employed. Cloned genes of the present invention, or fragments thereof, may also be used in gene therapy carded out homologous recombination or site-directed mutagenesis. See generally Thomas & Capecchi, 1987, *Cell* 51: 503–512; Bertling, 1987, *Bioscience Reports* 7: 107–112; Smithies et al., 1985, *Nature* 317: 230–234.

Oligonucleotides of the present invention are useful as diagnostic tools for probing MSH receptor gene expression in tissues. For example, tissues can be probed in situ with oligonucleotide probes carrying detectable groups by conventional autoradiography techniques, as explained in greater detail in the Examples below, to investigate native expression of this receptor or pathological conditions relating thereto. Further, chromosomes can be probed to investigate the presence or absence of the MSH-R gene, and potential pathological conditions related thereto, as also illustrated by the Examples below.

The invention also provides antibodies that are immunologically reactive to a mammalian MSH-R. The antibodies provided by the invention can be raised in animals by inoculation with cells that express a mammalian MSH-R or epitopes of a mammalian MSH-R using methods well known in the art. Animals that can be used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses a mammalian MSH-R, or any cell or cell line that expresses a mammalian MSH-R or any epitope therein as a result of molecular or genetic engineering, or that has been treated to increase the expression of a mammalian MSH-R by physical, biochemical or genetic means. Preferred cells are human cells, most preferably human 293 cells that have been transformed with a recombinant expression construct comprising DNA sequences encoding a mammalian MSH-R and that express the mammalian MSH-R gene product.

The present invention provides monoclonal antibodies that are immunologically reactive with an epitope that is a mammalian MSH-R present on the surface of mammalian cells, preferably human or mouse cells. These antibodies are made using methods and techniques well known to those of skill in the art.

Monoclonal antibodies provided by the present invention are produced by hybridoma cell lines, that are also provided by the invention and that are made by methods well known in the art. Hybridoma cell lines are made by fusing individual cells of a myeloma cell line with spleen cells derived from animals immunized with cells expressing a mammalian MSH-R, including human cells, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma calls can be injected subcutaneously and/or into the peritoneal cavity of an animal, most preferably a mouse, and the monoclonal antibodies obtained from blood and/or ascites fluid.

Monoclonal antibodies provided by the present invention can also be produced by recombinant genetic methods well known to those of skill in the art, and the present invention encompasses antibodies made by such methods that are immunologically reactive with an epitope of a mammalian MSH-R.

The present invention encompasses fragments of the antibody that are immunologically reactive with an epitope of a mammalian MSH-R. Such fragments can be produced by any number of methods, including but not limited to proteolytic cleavage, chemical synthesis or preparation of such fragments by means of genetic engineering technology. The present invention also encompasses single-chain antibodies that are immunologically reactive with an epitope of a mammalian MSH-R made by methods known to those of skill in the art.

The present invention also encompasses an epitope of a mammalian MSH-R that is comprised of sequences and/or a conformation of sequences present in the mammalian MSH-R molecule. This epitope may be naturally occurring, or may be the result of proteolytic cleavage of the mammalian MSH-R molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of immunologically reactive light chain and heavy chain peptides to an epitope that is a mammalian MSH-R. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They are set forth for explanatory purpose only, and are not to be taken as limiting the invention.

EXAMPLE 1

Isolation of an αMSH Receptor Probe by Random PCR Amplification of Human Melanoma cDNA Using Degenerate Oligonucleotide Primers In order to clone novel G-protein coupled receptors, human melanoma cDNA was used as template for a polymerase chain reaction (PCR)-based random cloning experiment. PCR was performed using a pair of degenerate oligonucleotide primers corresponding to the putative third and sixth transmembrane regions of G-protein coupled receptors (Libert et al., 1989, *Science* 244: 569–72; Zhou et al. 1990, *Nature* 347: 76–80). The PCR products obtained in this experiment were characterized by nucleotide sequencing. Two novel sequences representing novel G-protein-coupled receptors were identified.

PCR amplification was performed as follows. Total RNA was isolated from a human melanoma tumor sample by the guanidinium thiocyanate method (Chirgwin et al., 1979, *Biochemistry* 18: 5294–5299). Double-stranded cDNA was synthesized from total RNA with murine reverse transcriptase (BRL, Gaithersburg, Md.) by oligo-dT priming (Maniatis et al., *Molecular Cloning: A Laboratory Manual*, (Cold Spring Harbon Laboratory Press, Cold Spring Harbon, N.Y.), 1990). The melanoma cDNA mixture was then subjected to 45 cycles of PCR amplification using 500 picomoles of degenerate oligonucleotide primers having the following sequence:

Primer III (sense): (SEQ ID NO: 1)
GAGTCGACCTGTG(C/T)G(C/T)(C/G)AT(C/T)(A/G)CIIT(G/T)GAC(C/A)G(C/G)TAC Primer VI (antisense): (SEQ ID NO: 2)
CAGAATTCAG(T/A)AGGGCAICCAGCAGAI(G/C)(G/A)(T/C)GAA in 100 μl of a solution containing 50 mM Tris-HCl (pH 8.3), 2.5 mM MgCl$_2$, 0.01% gelatin, 200 μM each dNTP, and 2.5 units of Taq polymerase (Saiki et al., 1988, *Science* 239: 487–491). These primers were commercially synthesized by Research Genetics Inc. (Huntsville, Al.). Each PCR amplification cycle consisted of incubations at 94° C. for 1 min (denaturation), 45° C. for 2 min (annealing), and 72° C. for 2 min (extension).

Amplified products of the PCR reaction were extracted with phenol/chloroform and precipitated with ethanol. After digestion with EcoRI and SalI, the PCR products were separated on a 1.2% agarose gel. A slice of this gel, corresponding to PCR products of 300 basepairs (bp) in size, was cut out and purified using glass beads and sodium iodide, and the insert was then cloned into a pBKS cloning vector (Strategene, LaJolla, Calif.).

A total of 172 of such pBKS clones containing inserts were sequenced using Sequenase (U.S. Biochemical Corp., Cleveland, Ohio) by the dideoxynucleotide chain termination method (Sanger et al., 1977, *Proc. Natl. Acad. Sci. USA* 74: 5463–5467). Two types of sequences homologous to other G-protein coupled receptors were identified.

EXAMPLE 2

Isolation and Sequence Analysis of Mouse αMSH Receptor cDNA

Probes isolated in Example 1 were used to screen a *Cloudman melanoma* cDNA library in order to isolate a full-length cDNA corresponding to the cloned probe. One clone was isolated from a library of $5 \times 10^6$ clones screened as described below. This clone contained an insert of 2.6 kilobases (kb). The nucleotide sequence of the complete coding region was determined, as shown in FIG. 1A (SEQ ID NO:3).

The PCR probe was labeled by the random-priming method (Stratagene Primelt, #300387, LaJolla, Calif.) and used to screen a *Cloudman melanoma* line cDNA library constructed in the λZAP vector (Stratagene). Library screening was performed using techniques well-known in the art as described in Bunzow et al. (1988, *Nature* 336: 783–787) at moderate stringency (40% formamide, 1M NaCl, 50 mM Tris-HCl, pH 7.5, 0.1% sodium pyrophosphate, 0.2% sodium dodecyl sulfate, 100 µg/ml salmon sperm DNA, 10X Denhardt's solution). One cDNA clone was identified (termed mmdA) and its 2.6 kb cDNA insert was isolated and subcloned into pBKS (Stratagene); the resulting plasmid was called pmmelA. Nucleotide sequence analysis and homology comparisons were done on the OHSU computer system with software provided by Intelligenetics Inc. (Mountain View, Calif.).

The nucleotide sequence of pmmelA (the cDNA clone isolated a described above) is shown in FIG. 1A (SEQ ID NO:3). The longest open reading frame to this cDNA encodes a predicted protein product of 315 amino acids with a calculated molecular weight of 35.3 kilodaltons (kD). The deduced amino acid sequence is shown in FIG. 2 (SEQ ID NO:4) as mouse MSH-R. Single letter amino acid codes are used (see, G. Zubay, Biochemistry (2d ed.) 1988 (MacMillen Publishing: New York) p.33). Uppercase lettering indicates amino acid residues in common between the receptor proteins shown; lowercase lettering indicates divergent residues.

Hydrophobicity analysis (Kyte & Doolittle, 1982, *J. Mol. Biol.* 157: 105–132 of the deduced amino acid sequence showed that the protein contains seven hydrophobic stretches of 21 to 26 amino acids apiece. Putative transmembrane domains are overlined and designated with Roman numerals.

EXAMPLE 3

Construction of Mouse αMSH-R Expression Plasmids, DNA Transfection and Functional Expression of the αMSH-R Gene Product In order to biochemically characterize the putative mouse αMSH-R cDNA isolated as in Example 2, and to confirm that it encodes an αMSH receptor, mmelA was cloned into a mammalian expression vector, this vector transfected into human 293 cells, and cell lines generated that expressed the putative αMSH-R receptor at the cell surface. Such cells and membranes isolated from such cells were used for biochemical characterization experiments described below.

The entire coding region of the αMSH-R cDNA insert from mmelA contained in a 2.1 kb fragment was excised from pBSK and subcloned into the BamHI/XhoI sites of pcDNA/neo expression vector (Invitrogen, San Diego, Calif.). The resulting plasmid was called pcDNA-mmelA. pcDNA-mmelA plasmid DNA was prepared in large-scale through one cycle of CsCl gradient ultracentrifugation and 20 µg pcDNA-mmel DNA were transfected into each 100 mm dish of 293 cells using the calcium phosphate method (see Chen & Okayama, 1987, *Mol. Cell. Biol.* 7: 2745–2752). After transfection, cells were cultured in DMEM media supplemented with 10% calf serum in a 3% $CO_2$ atmosphere at 37° C. Selection was performed with neomycin (G418; GIBCO) at a concentration of 1000 µg/ml; selection was started 72 hr after transfection and continued for 3 weeks.

The αMSH-R is known to couple to G-proteins and thereby activate adenyl cyclase, increasing intracellular levels of cAMP (see Buckley & Ramachandran, 1981, *Proc. Natl. Acad. Sci. USA* 78: 7431–7435; Grahame-Smith et al., 1967, *J. Biol. Chem.* 242: 5535–5541; Mertz & Catt, 1991, *Proc. Natl. Acad. Sci. USA* 88: 8525–8529; Pawalek et al., 1976, *Invest. Dermatol.* 66: 200–209). This property of cells expressing the αMSH receptor was used analyze expression of the αMSH receptor in cell colonies transfected with the expression vectors described herein as follows. Cells (~1× $10^6$) were plated in 6-well dishes, washed once with DMEM containing 1% bovine serum albumin (BSA) and 0.5 mM IBMX (a phosphodiesterase inhibitor), then incubated for 45 minutes at 37° C. with varying concentrations of the melanotropic peptides αMSH, αMSH, γMSH, the MSH peptide analogues Nle$^4$, D-Phe$^7$-αMSH (NDP-MSH), and ACTH. Following hormone treatment, the cells were washed twice with phosphate buffered saline and intracellular cAMP extracted by lysing the cells with 1 ml of 60% ethanol. Intracellular cAMP concentrations were determined using an assay (Amersham) which measures the ability of cAMP to displace (8-$^3$H) cAMP from a high affinity cAMP binding protein (see Gilman, 1970, *Proc. Natl. Acad. Sci. USA* 67: 305–312).

The results of these experiments are shown in FIG. 3. The abscissa indicates the concentration of each hormone and the ordinate indicates the percentage of basal intracellular cAMP concentration achieved by each treatment. Points indicate the mean of duplicate incubations; the standard error did not exceed 15% for any data point. None of the peptides tested induced any change in intracellular cAMP in cells containing the vector alone. Cells expressing the murine αMSH receptor responded to melanotropic peptides with a 2–3 fold elevation of intracellular cAMP, similar to levels of cAMP induced by these peptides in the Cloudman cell line (see Pawalek, 1985, *Yale J Biol. Med.* 58: 571–578). The EC$_{50}$ values determined for αMSH ($2.8\times10^{-9}$M), ACTH ($8.0\times10^{-9}$M) and the superpotent MSH analogue NDP-MSH ($2.8\times10^{-11}$M) correspond closely to reported values (see Tatro et al., 1990, *Cancer Res.* 50: 1237–1242). As expected, the βMSH peptide had an EC$_{50}$ value comparable to αMSH, while γMSH had little or no activity (see Slominski et al., 1992, *Life Sci.* 50: 1103–1108), confirming the identity of this receptor as a melanocyte αMSH receptor.

EXAMPLE 4

Isolation and Characterization of a Human αMSH-R Genomic Clone

In order to isolate a human counterpart of the murine melanocyte αMSH receptor gene, a human genomic library was screened at high stringency (50% formamide, 42° C.) using the human PCR fragments isolated as described in Example 1. Two different types of sequences were isolated, corresponding to the two PCR fragments, and were found to encode highly related G protein-couple receptors. These genomic clones were sequenced as described in Example 2. One of these genomic clones was determined to encode a human MSH receptor (SEQ ID NO:5). The human MSH receptor has a predicted amino acid sequence (SEQ ID NO:6) that is 75% identical and colinear with the mouse αMSH receptor cDNA sequence (FIG. 2), represented as human MSH-R. The predicted molecular weight of the human MSH-R is 34.7 kD.

The predicted amino acid sequences of the mouse αMSH-R (SEQ ID NO:4) and human MSH-R (SEQ ID NO:6) are aligned in FIG. 2. These sequences define the melanocortin receptors as a novel subfamily of the G protein-coupled receptors with a number of unusual features. The melanocortin receptors are the smallest G protein-coupled receptors identified to date (297–317aa) resulting from a short amino terminal extracellular domain, a short carboxy-terminal intracellular domain, and a very small third intracellular loop. The melanocortin receptors lack several amino acid residues present in most G protein coupled receptors (see Probst et al., 1992, *DNA & Cell Biol.* 11: 1–20), including the proline residues in the 4$^{th}$ and 5$^{th}$ transmembrane domains, likely to introduce a bend in the alpha helical structure of the transmembrane domains and thought to be involved in the formation of the binding pocket (see Applebury & Hargrave, 1986, *Vision Res.* 26: 1881–1895), and one or both of the cysteine residues thought to form a disulfide bond between the first and second extracellular loops (see Dixon et al., 1987, *EMBO J.* 6: 3269–3275 and Karnik et al., 1988, *Proc. Natl. Acad. Sci. USA* 85: 8459–8463). Remarkably, the melanocortin receptors do not appear highly related to the other G protein-coupled receptors which recognize peptide ligands, such as the receptors for bombesin (see Spindel et al., 1990, *Mol. Endocrinol.* 4: 1956–1963) or substance K (see Masu et al., 1987, *Nature* 329: 836–838) but rather are more closely related to the receptor for $\Delta^9$-tetrahydrocannabinol (see Matsuda et al., 1990, *Nature* 346: 561–564). The cannabinoid receptor also lacks the conserved proline in transmembrane 5 and the cysteine in the first extracellular loop necessary for disulfide bond formation. Least parsimony analysis with the receptor sequences shown in FIG. 2 suggests the cannabinoid and melanocortin receptors may be evolutionarily related and form a subfamily distinct from the peptide receptors and the amine receptors. Regardless of whether the similarities are the result of evolutionary conservation or convergence, the sequence and putative structural similarities between the melanocortin and cannabinoid receptors may be informative in the search for the endogenous cannabinoid-like ligand.

EXAMPLE 5

Tissue Distribution of αMSH Receptors

Figure 4A:
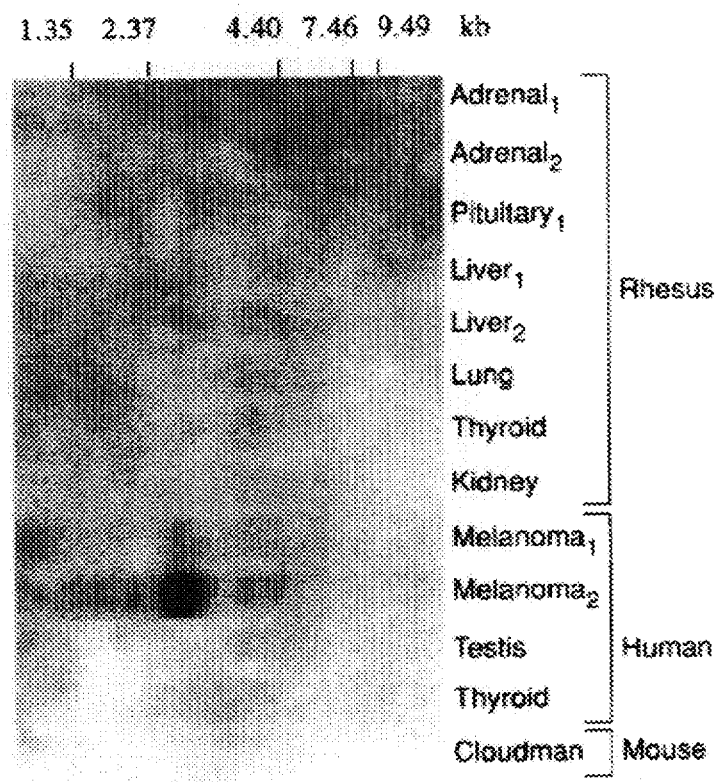
FIGS. 4A and 4B illustrate the tissue distribution of human (FIG. 4A) and mouse (FIG. 4B) melanocyte stimulating hormone receptor gene expression by Northern blot hybridization.
Figure 4B:
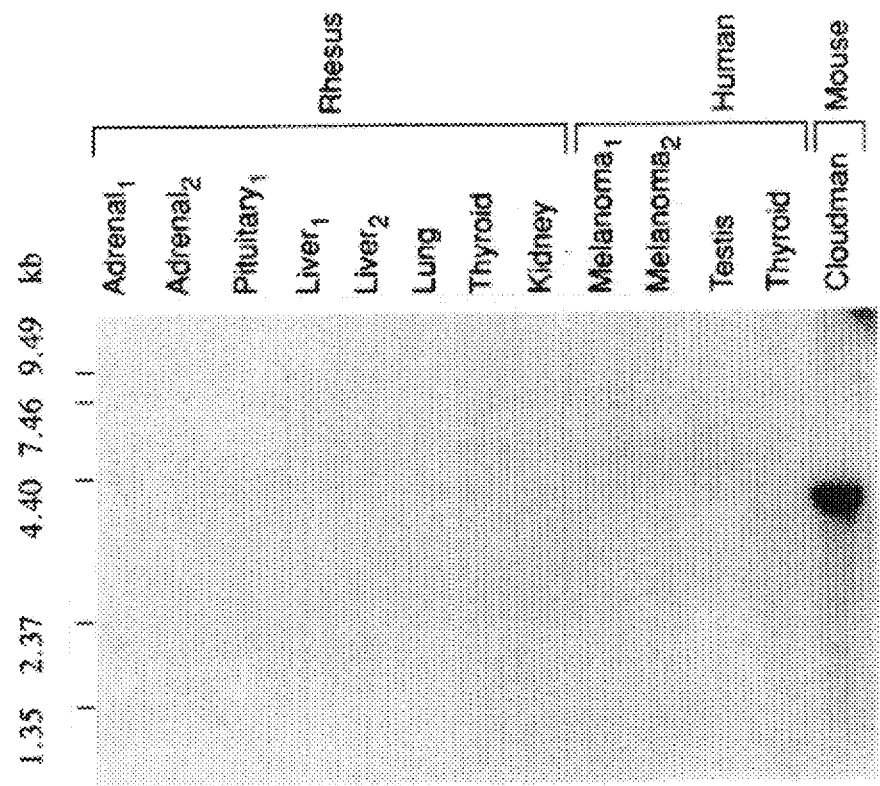

To further gain insight into these receptors, we have examined the tissue distribution of their corresponding mRNAs from various tissues by performing Northern hybridization experiments on RNA isolated from various tissues (see Maniatis et al., ibid.). The results of these experiments are shown in FIGS. 4A and 4B.

A panel of tissue samples was examined by Northern hybridization analysis performed under high stringency conditions. The same nitrocellulose filter was hybridized successively with a human MSH receptor probe and a mouse MSH receptor probe to determine the distribution of each receptor mRNA. The murine MSH receptor is encoded predominantly by a single mRNA species of 3.9 kb, while the human MSH receptor is encoded, in two melanoma samples, predominantly by a 3.0 kb species. High levels of receptor mRNA are seen in both primary mouse melanocytes and mouse melanoma cell lines. In contrast, extremely low levels of receptor mRNA were detected in primary human melanocytes, and many human melanoma samples (see melanoma 1, FIG. 4A). Most intriguing is the dramatic elevation of MSH-R mRNA seen thus far in 3 of 11 samples tested, such as is seen in melanoma sample #2 (FIG. 4A).

Additionally, we have been unable to detect expression in the brain of any of the receptors described here, despite extensive documentation of MSH binding sites there as well as in other tissues. These finding suggest that existence of alternate forms of these or related receptors that may be specifically expressed in brain tissue.

It should be understood that the foregoing disclosure emphasizes certain specific embodiments of the invention and that all modifications or alternatives equivalent thereto are within the spirit and scope of the invention as set forth in the appended claims.

---

What we claim is:

1. A homogeneous composition of a recombinantly-produced 35.3 kilodalton melanocyte stimulating hormone receptor, having an amino acid sequence identified as SEQ ID No.: 4.

2. A homogeneous composition of a recombinantly-produced 34.6 kilodalton melanocyte stimulating hormone receptor, having an amino acid sequence identified as SEQ ID No.: 6.

3. A homogeneous composition of a 35.3 kilodalton melanocyte stimulating hormone receptor produced by expressing in a cell a recombinant expression vector encoding a melanocyte stimulating hormone receptor having an amino acid sequence identified as SEQ ID No.:4.

4. A homogeneous composition of a 34.6 kilodalton melanocyte stimulating hormone receptor produced by expressing in a cell a recombinant expression vector encoding a melanocyte stimulating hormone receptor having an amino acid sequence identified as SEQ ID No.:6.

5. A cell membrane preparation comprising a 35.3 kilodalton melanocyte stimulating hormone receptor produced by a cell that expresses a recombinant expression vector encoding said melanocyte stimulating hormone receptor having an amino acid sequence identified as SEQ ID No.:4.

6. A cell membrane preparation comprising a 34.6 kilodalton melanocyte stimulating hormone receptor produced by a cell that expresses a recombinant expression vector encoding said melanocyte stimulating hormone receptor having an amino acid sequence identified as SEQ ID No.:6.

7. A homogeneous composition of a recombinantly-produced mammalian α-melanocyte stimulating hormone receptor, wherein said melanocyte stimulating hormone receptor has a molecular weight of about 35 kilodaltons and activates cAMP production in response to a melanotropic peptide selected from the group consisting of NDP-MSH, αMSH and ACTH.

8. A homogeneous composition of a mammalian α-melanocyte stimulating hormone receptor produced by a cell that expresses a recombinant expression vector encoding said α-melanocyte stimulating hormone receptor, said receptor having a molecular weight of about 35 kilodaltons and that activates cAMP production in response to a melanotropic peptide selected from the group consisting of NDP-MSH, αMSH and ACTH.

9. A cell membrane preparation comprising a mammalian α-melanocyte stimulating hormone receptor produced by a cell that expresses a recombinant expression vector encoding said α-melanocyte stimulating hormone receptor, said receptor having a molecular weight of about 35 kilodaltons and that activates cAMP production in response to a melanotropic peptide selected from the group consisting of NDP-MSH, αMSH and ACTH.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..35
        ( D ) OTHER INFORMATION: /function ="Degenerate
            oligonucleotide primer (sense)"
            / note= "The residue at positions 23 and 24 are
            inosine"

( x i ) SEQUENCE DESCRIPTION: SEQ ID NO:1:

GAGTCGACCT GTGYGYSATY RCNNTKGACM GSTAC        35

( 2 ) INFORMATION FOR SEQ ID NO:2:

( i ) SEQUENCE CHARACTERISTICS:

(A) LENGTH: 32 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: mics_feature
(B) LOCATION: 1..32
(D) OTHER INFORMATION: /function ="Degenerate oligonucleotide primer (antisense)"
/ note= "The residue at position 18 is inosine"

(xi) SEQUENCE DESCRIPTION: SEQ ID NO:2:

CAGAATTCAG WAGGGCANCC AGCAGASRYG AA　　　　　　　　　　　　　　　　　32

(2) INFORMATION FOR SEQ ID NO:3:

(i) SEQUENCE CHARACTERISTICS:
(A) LENGTH: 1260 base pairs
(B) TYPE: nucleic acid
(C) STRANDEDNESS: single
(D) TOPOLOGY: linear (ii) MOLECULE TYPE: cDNA to mRNA (ix) FEATURE:
(A) NAME/KEY: 5'UTR
(B) LOCATION: 1..14

(ix) FEATURE:
(A) NAME/KEY: CDS
(B) LOCATION: 15..959

(ix) FEATURE:
(A) NAME/KEY: 3'UTR
(B) LOCATION: 960..1260

(xi) SEQUENCE DESCRIPTION: SEQ ID NO:3:

```
TTCCTGACAA GACT ATG TCC ACT CAG GAG CCC CAG AAG AGT CTT CTG GGT            50
              Met Ser Thr Gln Glu Pro Gln Lys Ser Leu Leu Gly
              1           5                   10

TCT CTC AAC TCC AAT GCC ACC TCT CAC CTT GGA CTG GCC ACC AAC CAG            98
Ser Leu Asn Ser Asn Ala Thr Ser His Leu Gly Leu Ala Thr Asn Gln
        15              20                  25

TCA GAG CCT TGG TGC CTG TAT GTG TCC ATC CCA GAT GGC CTC TTC CTC           146
Ser Glu Pro Trp Cys Leu Tyr Val Ser Ile Pro Asp Gly Leu Phe Leu
    30              35              40

AGC CTA GGG CTG GTG AGT CTG GTG GAG AAT GTG CTG GTT GTG ATA GCC           194
Ser Leu Gly Leu Val Ser Leu Val Glu Asn Val Leu Val Val Ile Ala
45              50                  55                      60

ATC ACC AAA AAC CGC AAC CTG CAC TCG CCC ATG TAT TAC TTC ATC TGC           242
Ile Thr Lys Asn Arg Asn Leu His Ser Pro Met Tyr Tyr Phe Ile Cys
                65              70                      75

TGC CTG GCC CTG TCT GAC CTG ATG GTA AGT GTC AGC ATC GTG CTG GAG           290
Cys Leu Ala Leu Ser Asp Leu Met Val Ser Val Ser Ile Val Leu Glu
            80              85                  90

ACT ACT ATC ATC CTG CTG CTG GAG GTG GGC ATC CTG GTG GCC AGA GTG           338
Thr Thr Ile Ile Leu Leu Leu Glu Val Gly Ile Leu Val Ala Arg Val
        95              100                 105

GCT TTG GTG CAG CAG CTG GAC AAC CTC ATT GAC GTG CTC ATC TGT GGC           386
Ala Leu Val Gln Gln Leu Asp Asn Leu Ile Asp Val Leu Ile Cys Gly
    110             115                 120

TCC ATG GTG TCC AGT CTC TGC TTC CTG GGC ATC ATT GCT ATA GAC CGC           434
Ser Met Val Ser Ser Leu Cys Phe Leu Gly Ile Ile Ala Ile Asp Arg
125             130                 135                     140

TAC ATC TCC ATC TTC TAT GCG CTG CGT TAT CAC AGC ATC GTG ACG CTG           482
```

-continued

```
Tyr Ile Ser Ile Phe Tyr Ala Leu Arg Tyr His Ser Ile Val Thr Leu
            145                 150                 155

CCC AGA GCA CGA CGG GCT GTC GTG GGC ATC TGG ATG GTC AGC ATC GTC    530
Pro Arg Ala Arg Arg Ala Val Val Gly Ile Trp Met Val Ser Ile Val
            160                 165                 170

TCC AGC ACC CTC TTT ATC ACC TAC TAC AAG CAC ACA GCC GTT CTG CTC    578
Ser Ser Thr Leu Phe Ile Thr Tyr Tyr Lys His Thr Ala Val Leu Leu
        175                 180                 185

TGC CTC GTC ACT TTC TTT CTA GCC ATG CTG GCA CTC ATG GCG ATT CTG    626
Cys Leu Val Thr Phe Phe Leu Ala Met Leu Ala Leu Met Ala Ile Leu
        190                 195                 200

TAT GCC CAC ATG TTC ACG AGA GCG TGC CAG CAC GTC CAG GGC ATT GCC    674
Tyr Ala His Met Phe Thr Arg Ala Cys Gln His Val Gln Gly Ile Ala
205                 210                 215                 220

CAG CTC CAC AAA AGG CGG CGG TCC ATC CGC CAA GGC TTC TGC CTC AAG    722
Gln Leu His Lys Arg Arg Arg Ser Ile Arg Gln Gly Phe Cys Leu Lys
                225                 230                 235

GGT GCT GCC ACC CTT ACT ATC CTT CTG GGG ATT TTC TTC CTG TGC TGG    770
Gly Ala Ala Thr Leu Thr Ile Leu Leu Gly Ile Phe Phe Leu Cys Trp
            240                 245                 250

GGC CCC TTC TTC CTG CAT CTC TTG CTC ATC GTC CTC TGC CCT CAG CAC    818
Gly Pro Phe Phe Leu His Leu Leu Leu Ile Val Leu Cys Pro Gln His
        255                 260                 265

CCC ACC TGC AGC TGC ATC TTC AAG AAC TTC AAC CTC TTC CTC CTC CTC    866
Pro Thr Cys Ser Cys Ile Phe Lys Asn Phe Asn Leu Phe Leu Leu Leu
        270                 275                 280

ATC GTC CTC AGC TCC ACT GTT GAC CCC CTC ATC TAT GCT TTC CGC AGC    914
Ile Val Leu Ser Ser Thr Val Asp Pro Leu Ile Tyr Ala Phe Arg Ser
285                 290                 295                 300

CAG GAG CTC CGC ATG ACA CTC AAG GAG GTG CTG CTG TGC TCC TGG        959
Gln Glu Leu Arg Met Thr Leu Lys Glu Val Leu Leu Cys Ser Trp
                305                 310                 315

TGATCAGAGG GCGCTGGGCA GAGGGTGACA GTGATATCCA GTGGCCTGCA TCTGTGAGAC   1019

CACAGGTACT CATCCCTTCC TGATCTCCAT TTGTCTAAGG GTCGACAGGA TGAGCTTTAA   1079

AATAGAAACC CAGAGTGCCT GGGGCCAGGA GAAAGGGTAA CTGTGACTGC AGGGCTCACC   1139

CAGGGCAGCT ACGGGAAGTG GAGGAGACAG GGATGGGAAC TCTAGCCCTG AGCAAGGGTC   1199

AGACCACAGG CTCCTGAAGA GCTTCACCTC TCCCCACCTA CAGGCAACTC CTGCTCAAGC   1259

C                                                                   1260
```

( 2 ) INFORMATION FOR SEQ ID NO:4:

( i ) SEQUENCE CHARACTERISTICS:
        ( A ) LENGTH: 315 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ser Thr Gln Glu Pro Gln Lys Ser Leu Leu Gly Ser Leu Asn Ser
 1               5                  10                  15

Asn Ala Thr Ser His Leu Gly Leu Ala Thr Asn Gln Ser Glu Pro Trp
            20                  25                  30

Cys Leu Tyr Val Ser Ile Pro Asp Gly Leu Phe Leu Ser Leu Gly Leu
        35                  40                  45

Val Ser Leu Val Glu Asn Val Leu Val Val Ile Ala Ile Thr Lys Asn
    50                  55                  60

Arg Asn Leu His Ser Pro Met Tyr Tyr Phe Ile Cys Cys Leu Ala Leu
```

| | | | | | | | | | | | | | | | |
|---|---|---|---|---|---|---|---|---|---|---|---|---|---|---|---|
| 65 | | | | | 70 | | | | 75 | | | | | 80 | |
| Ser | Asp | Leu | Met | Val 85 | Ser | Val | Ser | Ile 90 | Val | Leu | Glu | Thr | Thr | Ile 95 | Ile |
| Leu | Leu | Leu | Glu 100 | Val | Gly | Ile | Leu | Val 105 | Ala | Arg | Val | Ala | Leu 110 | Val | Gln |
| Gln | Leu | Asp 115 | Asn | Leu | Ile | Asp | Val 120 | Leu | Ile | Cys | Gly | Ser 125 | Met | Val | Ser |
| Ser | Leu 130 | Cys | Phe | Leu | Gly 135 | Ile | Ala | Ile | Asp | Arg 140 | Tyr | Ile | Ser | Ile |
| Phe 145 | Tyr | Ala | Leu | Arg | Tyr 150 | His | Ser | Ile | Val | Thr 155 | Leu | Pro | Arg | Ala | Arg 160 |
| Arg | Ala | Val | Val | Gly 165 | Ile | Trp | Met | Val | Ser 170 | Ile | Val | Ser | Ser 175 | Thr | Leu |
| Phe | Ile | Thr | Tyr 180 | Tyr | Lys | His | Thr | Ala 185 | Val | Leu | Leu | Cys | Leu 190 | Val | Thr |
| Phe | Phe | Leu 195 | Ala | Met | Leu | Ala | Leu 200 | Met | Ala | Ile | Leu | Tyr 205 | Ala | His | Met |
| Phe | Thr 210 | Arg | Ala | Cys | Gln | His 215 | Val | Gln | Gly | Ile | Ala 220 | Gln | Leu | His | Lys |
| Arg 225 | Arg | Arg | Ser | Ile | Arg 230 | Gln | Gly | Phe | Cys | Leu 235 | Lys | Gly | Ala | Ala | Thr 240 |
| Leu | Thr | Ile | Leu | Leu 245 | Gly | Ile | Phe | Phe | Leu 250 | Cys | Trp | Gly | Pro | Phe 255 | Phe |
| Leu | His | Leu | Leu 260 | Leu | Ile | Val | Leu | Cys 265 | Pro | Gln | His | Pro | Thr 270 | Cys | Ser |
| Cys | Ile | Phe 275 | Lys | Asn | Phe | Asn | Leu 280 | Phe | Leu | Leu | Leu | Ile 285 | Val | Leu | Ser |
| Ser | Thr 290 | Val | Asp | Pro | Leu | Ile 295 | Tyr | Ala | Phe | Arg | Ser 300 | Gln | Glu | Leu | Arg |
| Met 305 | Thr | Leu | Lys | Glu | Val 310 | Leu | Leu | Cys | Ser | Trp 315 | | | | | |

( 2 ) INFORMATION FOR SEQ ID NO:5:

( i ) SEQUENCE CHARACTERISTICS:
        ( A ) LENGTH: 1633 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY: 5'UTR
        ( B ) LOCATION: 1..461

( i x ) FEATURE:
        ( A ) NAME/KEY: CDS
        ( B ) LOCATION: 462..1415

( i x ) FEATURE:
        ( A ) NAME/KEY: 3'UTR
        ( B ) LOCATION: 1416..1633

( x i ) SEQUENCE DESCRIPTION: SEQ ID NO:5:

```
CCCGCATGTG GCCGCCCTCA ATGGAGGGCT CTGAGAACGA CTTTTAAAAC GCAGAGAAAA      60

AGCTCCATTC TTCCCAGACC TCAGCGCAGC CCTGGCCCAG GAAGGGAGGA GACAGAGGCC     120

AGGACGGTCC AGAGGTGTCG AAATGTCCTG GAACCTGAG CAGCAGCCAC CAGGGAAGAG      180

GCAGGGAGGG AGCTGAGGAC CAGGCTTGGT TGTGAGAATC CCTGAGCCCA GGCGGTTGAT     240
```

```
GCCAGGAGGT GTCTGGACTG GCTGGGCCAT GCCTGGGCTG ACCTGTCCAG CCAGGGAGAG       300

GGTGTGAGGG CAGATCTGGG GGTGCCCAGA TGGAAGGAGG CAGGCATGGG GACACCCAAG       360

GCCCCCTGGC AGCACCATGA ACTAAGCAGG ACACCTGGAG GGGAAGAACT GTGGGGACCT       420

GGAGGCCTCC AACGACTCCT TCCTGCTTCC TGGACAGGAC T ATG GCT GTG CAG           473
                                              Met Ala Val Gln
                                               1
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| GGA | TCC | CAG | AGA | AGA | CTT | CTG | GGC | TCC | CTC | AAC | TCC | ACC | CCC | ACA | GCC | 521 |
| Gly | Ser | Gln | Arg | Arg | Leu | Leu | Gly | Ser | Leu | Asn | Ser | Thr | Pro | Thr | Ala |     |
|  5  |     |     |     |  10 |     |     |     |     |  15 |     |     |     |     |  20 |     |     |

```
ATC CCC CAG CTG GGG CTG GCT GCC AAC CAG ACA GGA GCC CGG TGC CTG         569
Ile Pro Gln Leu Gly Leu Ala Ala Asn Gln Thr Gly Ala Arg Cys Leu
             25                  30                  35

GAG GTG TCC ATC TCT GAC GGG CTC TTC CTC AGC CTG GGG CTG GTG AGC         617
Glu Val Ser Ile Ser Asp Gly Leu Phe Leu Ser Leu Gly Leu Val Ser
             40                  45                  50

TTG GTG GAG AAC GCG CTG GTG GTG GCC ACC ATC GCC AAG AAC CGG AAC         665
Leu Val Glu Asn Ala Leu Val Val Ala Thr Ile Ala Lys Asn Arg Asn
             55                  60                  65

CTG CAC TCA CCC ATG TAC TGC TTC ATC TGC TGC CTG GCC TTG TCG GAC         713
Leu His Ser Pro Met Tyr Cys Phe Ile Cys Cys Leu Ala Leu Ser Asp
         70              75                  80

CTG CTG GTG AGC GGG ACG AAC GTG CTG GAG ACG GCC GTC ATC CTC CTG         761
Leu Leu Val Ser Gly Thr Asn Val Leu Glu Thr Ala Val Ile Leu Leu
 85              90                  95                 100

CTG GAG GCC GGT GCA CTG GTG GCC CGG GCT GCG GTG CTG CAG CAG CTG         809
Leu Glu Ala Gly Ala Leu Val Ala Arg Ala Ala Val Leu Gln Gln Leu
                 105                 110                 115

GAC AAT GTC ATT GAC GTG ATC ACC TGC AGC TCC ATG CTG TCC AGC CTC         857
Asp Asn Val Ile Asp Val Ile Thr Cys Ser Ser Met Leu Ser Ser Leu
             120                 125                 130

TGC TTC CTG GGC GCC ATC GCC GTG GAC CGC TAC ATC TCC ATC TTC TAC         905
Cys Phe Leu Gly Ala Ile Ala Val Asp Arg Tyr Ile Ser Ile Phe Tyr
             135                 140                 145

GCA CTG CGC TAC CAC AGC ATC GTG ACC CTG CCG CGG GCG CCG CGA GCC         953
Ala Leu Arg Tyr His Ser Ile Val Thr Leu Pro Arg Ala Pro Arg Ala
         150                 155                 160

GTT GCG GCC ATC TGG GTG GCC AGT GTC GTC TTC AGC ACG CTC TTC ATC        1001
Val Ala Ala Ile Trp Val Ala Ser Val Val Phe Ser Thr Leu Phe Ile
165              170                 175                 180

GGC TAC TAC GAC CAC GTG GCC GTC CTG CTG TGC CTC GTG GTC TTC TTC        1049
Gly Tyr Tyr Asp His Val Ala Val Leu Leu Cys Leu Val Val Phe Phe
                 185                 190                 195

CTG GCT ATG CTG GTG CTC ATG GCC GTG CTG GAC GTC CAC ATG CTG GCC        1097
Leu Ala Met Leu Val Leu Met Ala Val Leu Asp Val His Met Leu Ala
             200                 205                 210

CGG GCC TGC CAG CAC GCC CAG GGC ATC GCC CGG CTC CAC AAG AGG CAG        1145
Arg Ala Cys Gln His Ala Gln Gly Ile Ala Arg Leu His Lys Arg Gln
             215                 220                 225

CGC CCG GTC CAC CAG GGC TTT GGC CTT AAA GGC GCT GTC ACC CTC ACC        1193
Arg Pro Val His Gln Gly Phe Gly Leu Lys Gly Ala Val Thr Leu Thr
         230                 235                 240

ATC CTG CTG GGC ATT TTC TTC CTC TGC TGG GGC CCC TTC TTC CTG CAT        1241
Ile Leu Leu Gly Ile Phe Phe Leu Cys Trp Gly Pro Phe Phe Leu His
245                  250                 255                 260

CTC ACA CTC ATC GTC CTC TGC CCC GAG CAC CCC ACG TGC GGC TGC ATC        1289
Leu Thr Leu Ile Val Leu Cys Pro Glu His Pro Thr Cys Gly Cys Ile
             265                 270                 275

TTC AAG AAC TTC AAC CTC TTT CTC GCC CTC ATC ATC TGC AAT GCC ATC        1337
Phe Lys Asn Phe Asn Leu Phe Leu Ala Leu Ile Ile Cys Asn Ala Ile
```

```
                              280                           285                           290
ATC  GAC  CCC  CTC  ATC  TAC  GCC  TTC  CAC  AGC  CAG  GAG  CTC  CGC  AGG  ACG         1385
Ile  Asp  Pro  Leu  Ile  Tyr  Ala  Phe  His  Ser  Gln  Glu  Leu  Arg  Arg  Thr
          295                      300                           305

CTC  AAG  GAG  GTG  CTG  ACA  TGC  TCC  TGG  TGA  GCGCGGTGCA  CGCGCTTTAA               1435
Leu  Lys  Glu  Val  Leu  Thr  Cys  Ser  Trp  *
     310                           315

GTGTGCTGGG  CAGAGGGAGG  TGGTGATATT  GTGGTCTGGT  TCCTGTGTGA  CCCTGGGCAG                 1495

TTCCTTACCT  CCCTGGTCCC  CGTTTGTCAA  AGAGGATGGA  CTAAATGATC  TCTGAAAGTG                 1555

TTGAAGCGCG  GACCCTTCTG  GGCAGGGAGG  GGTCCTGCAA  AACTCCAGGC  AGGACTTCTC                 1615

ACCAGCAGTC  GTGGGAAC                                                                   1633
```

( 2 ) INFORMATION FOR SEQ ID NO:6:

( i ) SEQUENCE CHARACTERISTICS:
        ( A ) LENGTH: 317 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ala  Val  Gln  Gly  Ser  Gln  Arg  Arg  Leu  Leu  Gly  Ser  Leu  Asn  Ser
 1                        5                       10                       15

Thr  Pro  Thr  Ala  Ile  Pro  Gln  Leu  Gly  Leu  Ala  Ala  Asn  Gln  Thr  Gly
               20                       25                       30

Ala  Arg  Cys  Leu  Glu  Val  Ser  Ile  Ser  Asp  Gly  Leu  Phe  Leu  Ser  Leu
          35                       40                       45

Gly  Leu  Val  Ser  Leu  Val  Glu  Asn  Ala  Leu  Val  Val  Ala  Thr  Ile  Ala
     50                       55                       60

Lys  Asn  Arg  Asn  Leu  His  Ser  Pro  Met  Tyr  Cys  Phe  Ile  Cys  Cys  Leu
65                       70                       75                       80

Ala  Leu  Ser  Asp  Leu  Leu  Val  Ser  Gly  Thr  Asn  Val  Leu  Glu  Thr  Ala
                    85                       90                       95

Val  Ile  Leu  Leu  Leu  Glu  Ala  Gly  Ala  Leu  Val  Ala  Arg  Ala  Ala  Val
                    100                      105                      110

Leu  Gln  Gln  Leu  Asp  Asn  Val  Ile  Asp  Val  Ile  Thr  Cys  Ser  Ser  Met
          115                      120                      125

Leu  Ser  Ser  Leu  Cys  Phe  Leu  Gly  Ala  Ile  Ala  Val  Asp  Arg  Tyr  Ile
     130                      135                      140

Ser  Ile  Phe  Tyr  Ala  Leu  Arg  Tyr  His  Ser  Ile  Val  Thr  Leu  Pro  Arg
145                      150                      155                      160

Ala  Pro  Arg  Ala  Val  Ala  Ala  Ile  Trp  Val  Ala  Ser  Val  Val  Phe  Ser
               165                      170                      175

Thr  Leu  Phe  Ile  Gly  Tyr  Tyr  Asp  His  Val  Ala  Val  Leu  Leu  Cys  Leu
               180                      185                      190

Val  Val  Phe  Phe  Leu  Ala  Met  Leu  Val  Leu  Met  Ala  Val  Leu  Asp  Val
               195                      200                      205

His  Met  Leu  Ala  Arg  Ala  Cys  Gln  His  Ala  Gln  Gly  Ile  Ala  Arg  Leu
     210                      215                      220

His  Lys  Arg  Gln  Arg  Pro  Val  His  Gln  Gly  Phe  Gly  Leu  Lys  Gly  Ala
225                      230                      235                      240

Val  Thr  Leu  Thr  Ile  Leu  Leu  Gly  Ile  Phe  Phe  Leu  Cys  Trp  Gly  Pro
               245                      250                      255

Phe  Phe  Leu  His  Leu  Thr  Leu  Ile  Val  Leu  Cys  Pro  Glu  His  Pro  Thr
               260                      265                      270
```

```
Cys  Gly  Cys  Ile  Phe  Lys  Asn  Phe  Asn  Leu  Phe  Leu  Ala  Leu  Ile  Ile
     275                      280                     285

Cys  Asn  Ala  Ile  Ile  Asp  Pro  Leu  Ile  Tyr  Ala  Phe  His  Ser  Gln  Glu
     290                      295                     300

Leu  Arg  Arg  Thr  Leu  Lys  Glu  Val  Leu  Thr  Cys  Ser  Trp
305                      310                     315
```

( 2 ) INFORMATION FOR SEQ ID NO:7:

( i ) SEQUENCE CHARACTERISTICS:
        ( A ) LENGTH: 297 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Lys  His  Ile  Ile  Asn  Ser  Tyr  Glu  Asn  Ile  Asn  Asn  Thr  Ala  Arg
1                        5                        10                      15

Asn  Asn  Ser  Asp  Cys  Pro  Arg  Val  Val  Leu  Pro  Glu  Glu  Ile  Phe  Phe
          20                      25                      30

Thr  Ile  Ser  Ile  Val  Gly  Val  Leu  Glu  Asn  Leu  Ile  Val  Leu  Leu  Ala
          35                      40                      45

Val  Phe  Lys  Asn  Lys  Asn  Leu  Gln  Ala  Pro  Met  Tyr  Phe  Phe  Ile  Cys
     50                      55                      60

Ser  Leu  Ala  Ile  Ser  Asp  Met  Leu  Gly  Ser  Leu  Tyr  Lys  Ile  Leu  Glu
65                       70                      75                       80

Asn  Ile  Leu  Ile  Ile  Leu  Arg  Asn  Met  Gly  Tyr  Leu  Lys  Pro  Arg  Gly
                    85                      90                      95

Ser  Phe  Glu  Thr  Thr  Ala  Asp  Asp  Ile  Ile  Asp  Ser  Leu  Phe  Val  Leu
               100                     105                     110

Ser  Leu  Leu  Gly  Ser  Ile  Phe  Asp  Leu  Ser  Val  Ile  Ala  Ala  Asp  Arg
               115                     120                     125

Tyr  Ile  Thr  Ile  Phe  His  Ala  Leu  Arg  Tyr  His  Ser  Ile  Val  Thr  Met
     130                     135                     140

Arg  Arg  Thr  Val  Val  Val  Leu  Thr  Val  Ile  Trp  Thr  Phe  Cys  Thr  Gly
145                      150                     155                      160

Thr  Gly  Ile  Thr  Met  Val  Ile  Phe  Ser  His  His  Val  Pro  Thr  Val  Ile
               165                     170                     175

Thr  Phe  Thr  Ser  Leu  Phe  Pro  Leu  Met  Leu  Val  Phe  Ile  Leu  Cys  Leu
               180                     185                     190

Tyr  Val  His  Met  Phe  Leu  Ile  Ala  Arg  Ala  His  Thr  Arg  Lys  Ile  Ser
     195                     200                     205

Thr  Leu  Pro  Arg  Ala  Asn  Met  Lys  Gly  Ala  Ile  Thr  Leu  Thr  Ile  Leu
210                      215                     220

Leu  Gly  Val  Phe  Ile  Phe  Cys  Trp  Ala  Pro  Phe  Val  Leu  His  Val  Leu
225                      230                     235                      240

Leu  Met  Thr  Phe  Cys  Pro  Ser  Asn  Pro  Tyr  Cys  Ala  Cys  Tyr  Met  Ser
               245                     250                     255

Leu  Phe  Gln  Val  Asn  Gly  Met  Leu  Ile  Met  Cys  Asn  Ala  Val  Ile  Asp
               260                     265                     270

Pro  Phe  Ile  Tyr  Ala  Phe  Arg  Ser  Pro  Glu  Leu  Arg  Asp  Ala  Phe  Lys
               275                     280                     285

Lys  Met  Ile  Phe  Cys  Ser  Arg  Tyr  Trp
290                      295
```

( 2 ) INFORMATION FOR SEQ ID NO:8:

( i ) SEQUENCE CHARACTERISTICS:
( A ) LENGTH: 470 amino acids
( B ) TYPE: amino acid
( D ) TOPOLOGY: linear ( i i ) MOLECULE TYPE: protein ( i x ) FEATURE:
( A ) NAME/KEY: misc_feature
( B ) LOCATION: 1..103
( D ) OTHER INFORMATION: /function ="Inserted sequence"
/ note= "An amino acid sequence insert of 101 amino acids is undisclosed between residues 1 and 103."

( i x ) FEATURE:
( A ) NAME/KEY: misc_feature
( B ) LOCATION: 285..317
( D ) OTHER INFORMATION: /function ="Inserted sequence"
/ note= "An amino acid sequence insert of 31 amino acids is undisclosed between residues 285 and 317."

( i x ) FEATURE:
( A ) NAME/KEY: misc_feature
( B ) LOCATION: 414
( D ) OTHER INFORMATION: /function ="Inserted sequence"
/ note= "An amino acid sequence insert of 56 amino acids is undisclosed at residue 414."

( x i ) SEQUENCE DESCRIPTION: SEQ ID NO:8:

```
Met Xaa Xaa Xaa Xaa Xaa Xaa Xaa Xaa Xaa Xaa Xaa Xaa Xaa Xaa Xaa
 1               5                  10                  15
Xaa Xaa Xaa Xaa Xaa Xaa Xaa Xaa Xaa Xaa Xaa Xaa Xaa Xaa Xaa Xaa
                20                  25                  30
Xaa Xaa Xaa Xaa Xaa Xaa Xaa Xaa Xaa Xaa Xaa Xaa Xaa Xaa Xaa Xaa
             35                  40                  45
Xaa Xaa Xaa Xaa Xaa Xaa Xaa Xaa Xaa Xaa Xaa Xaa Xaa Xaa Xaa Xaa
 50                  55                  60
Xaa Xaa Xaa Xaa Xaa Xaa Xaa Xaa Xaa Xaa Xaa Xaa Xaa Xaa Xaa Xaa
 65                  70                  75                  80
Xaa Xaa Xaa Xaa Xaa Xaa Xaa Xaa Xaa Xaa Xaa Xaa Xaa Xaa Xaa Xaa
                 85                  90                  95
Xaa Xaa Xaa Xaa Xaa Xaa Asn Asn Ser Asp Cys Pro Arg Val Val Leu
            100                 105                 110
Pro Glu Glu Leu Phe Leu Thr Leu Gly Ile Val Gly Val Leu Glu Asn
        115                 120                 125
Leu Leu Val Leu Leu Ala Ile Phe Lys Asn Arg Asn Leu Gln Ala Pro
130                 135                 140
Met Tyr Phe Phe Ile Cys Ser Leu Ala Ile Ser Asp Leu Leu Gly Ser
145                 150                 155                 160
Val Tyr Lys Val Leu Glu Asn Ile Leu Ile Ile Leu Arg Asn Met Gly
                165                 170                 175
Tyr Leu Lys Pro Arg Gly Ser Phe Glu Thr Thr Ala Asp Asp Ile Ile
            180                 185                 190
Asp Ser Leu Phe Val Leu Ser Leu Leu Gly Ser Ile Phe Asp Leu Ser
        195                 200                 205
Val Ile Ala Ile Asp Arg Tyr Ile Ser Ile Phe His Ala Leu Arg Tyr
210                 215                 220
His Ser Ile Val Thr Met Pro Arg Ala Val Val Ala Leu Thr Val Ile
225                 230                 235                 240
Trp Thr Phe Cys Ile Val Thr Gly Ile Leu Met Val Ile Phe Ser His
                245                 250                 255
```

-continued

| His | Val | Pro | Thr 260 | Val | Ile | Thr | Phe | Thr 265 | Ser | Leu | Phe | Pro | Leu 270 | Met | Leu |
|---|---|---|---|---|---|---|---|---|---|---|---|---|---|---|---|
| Val | Phe | Ile 275 | Leu | Cys | Leu | Tyr | Val 280 | His | Met | Phe | Leu | Ile 285 | Xaa | Xaa | Xaa |
| Xaa | Xaa 290 | Xaa | Xaa | Xaa | Xaa | Xaa 295 | Xaa | Xaa | Xaa | Xaa | Xaa 300 | Xaa | Xaa | Xaa | Xaa |
| Xaa 305 | Xaa | Xaa | Xaa | Xaa | Xaa 310 | Xaa | Xaa | Xaa | Xaa | Xaa 315 | Xaa | Ala | Arg | Ala | His 320 |
| Thr | Arg | Lys | Arg | Pro 325 | Thr | Leu | Pro | Arg | Ala 330 | Asn | Met | Lys | Gly | Ala 335 | Ile |
| Thr | Leu | Thr | Ile 340 | Leu | Leu | Gly | Val | Phe 345 | Ile | Phe | Cys | Trp | Gly 350 | Pro | Phe |
| Val | Leu | His 355 | Val | Leu | Leu | Met | Thr 360 | Phe | Cys | Pro | Ser | Asn 365 | Pro | Tyr | Cys |
| Ala | Cys 370 | Ile | Met | Ser | Leu | Phe 375 | Gln | Val | Asn | Gly | Met 380 | Leu | Ile | Met | Leu |
| Asn 385 | Ser | Thr | Val | Asp | Pro 390 | Phe | Ile | Tyr | Ala | Phe 395 | Arg | Ser | Pro | Glu | Leu 400 |
| Arg | Asp | Ala | Phe | Lys 405 | Lys | Met | Ile | Phe | Cys 410 | Ser | Arg | Tyr | Trp | Xaa 415 | Xaa |
| Xaa | Xaa | Xaa | Xaa 420 | Xaa | Xaa | Xaa | Xaa | Xaa 425 | Xaa | Xaa | Xaa | Xaa | Xaa 430 | Xaa | Xaa |
| Xaa | Xaa | Xaa 435 | Xaa | Xaa | Xaa | Xaa | Xaa 440 | Xaa | Xaa | Xaa | Xaa | Xaa 445 | Xaa | Xaa | Xaa |
| Xaa | Xaa 450 | Xaa | Xaa | Xaa | Xaa | Xaa 455 | Xaa | Xaa | Xaa | Xaa | Xaa 460 | Xaa | Xaa | Xaa | Xaa |
| Xaa 465 | Xaa | Xaa | Xaa | Xaa | Xaa 470 | | | | | | | | | | |